United States Patent
Sarek et al.

(10) Patent No.: US 8,093,413 B2
(45) Date of Patent: Jan. 10, 2012

(54) METHOD OF PREPARATION AND ISOLATION OF BETULIN DIACETATE FROM BIRCH BARK FROM PAPER MILLS AND ITS OPTICAL PROCESSING TO BETULIN

(75) Inventors: Jan Sarek, Horni Mecholupy (CZ); Michal Svoboda, Prague (CZ); Marian Hajduch, Moravsky Beroun (CZ)

(73) Assignees: Univerzita Karlova V Praze, Prirodovedecka Fakulta, Olomouc (CZ); Univerzita Palackeho V Olomouci and I.Q.A., a.s., Praha (CZ)

( * ) Notice: Subject to any disclaimer, the term of this patent is extended or adjusted under 35 U.S.C. 154(b) by 420 days.

(21) Appl. No.: 12/522,339

(22) PCT Filed: Jan. 9, 2008

(86) PCT No.: PCT/CZ2008/000004
§ 371 (c)(1),
(2), (4) Date: Jul. 7, 2009

(87) PCT Pub. No.: WO2008/086759
PCT Pub. Date: Jul. 24, 2008

(65) Prior Publication Data
US 2009/0318719 A1    Dec. 24, 2009

(30) Foreign Application Priority Data
Jan. 15, 2007    (CZ) ...................................... 2007-36

(51) Int. Cl.
*C07J 53/00*    (2006.01)
(52) U.S. Cl. ...................................................... 552/510
(58) Field of Classification Search .................. 552/510
See application file for complete search history.

*Primary Examiner* — Barbara P Badio
(74) *Attorney, Agent, or Firm* — Notaro, Michalos & Zaccaria P.C.

(57) ABSTRACT

The invention relates to a method of preparation and isolation of betulin diacetate from birch bark from paper mills and its optional processing to betulin, wherein the birch bark is ground, mixed with two- to twenty-fold excess volume of water and is stirred so that all birch bark is dipped, then the fraction of the birch bark which floats on the surface is collected, said collected fraction is dried at the temperature in the range of from 50 to 85° C. and the betulin contained in the dried birch bark is then subjected to an acetylation reaction, after the acetylation the birch bark is dried at the temperature of from 50 to 100° C. and the formed betulin diacetate is then isolated from the birch bark by supercritical extraction of the birch bark with carbon dioxide at the pressure of 28-35 MPa and the temperature of from 50 to 100° C. and subsequently, the supercritical extract is recrystallized for direct use or for further processing. The further processing can be basic hydrolysis of the re-crystallized betulin diacetate to betulin.

12 Claims, 1 Drawing Sheet

Figure 1:
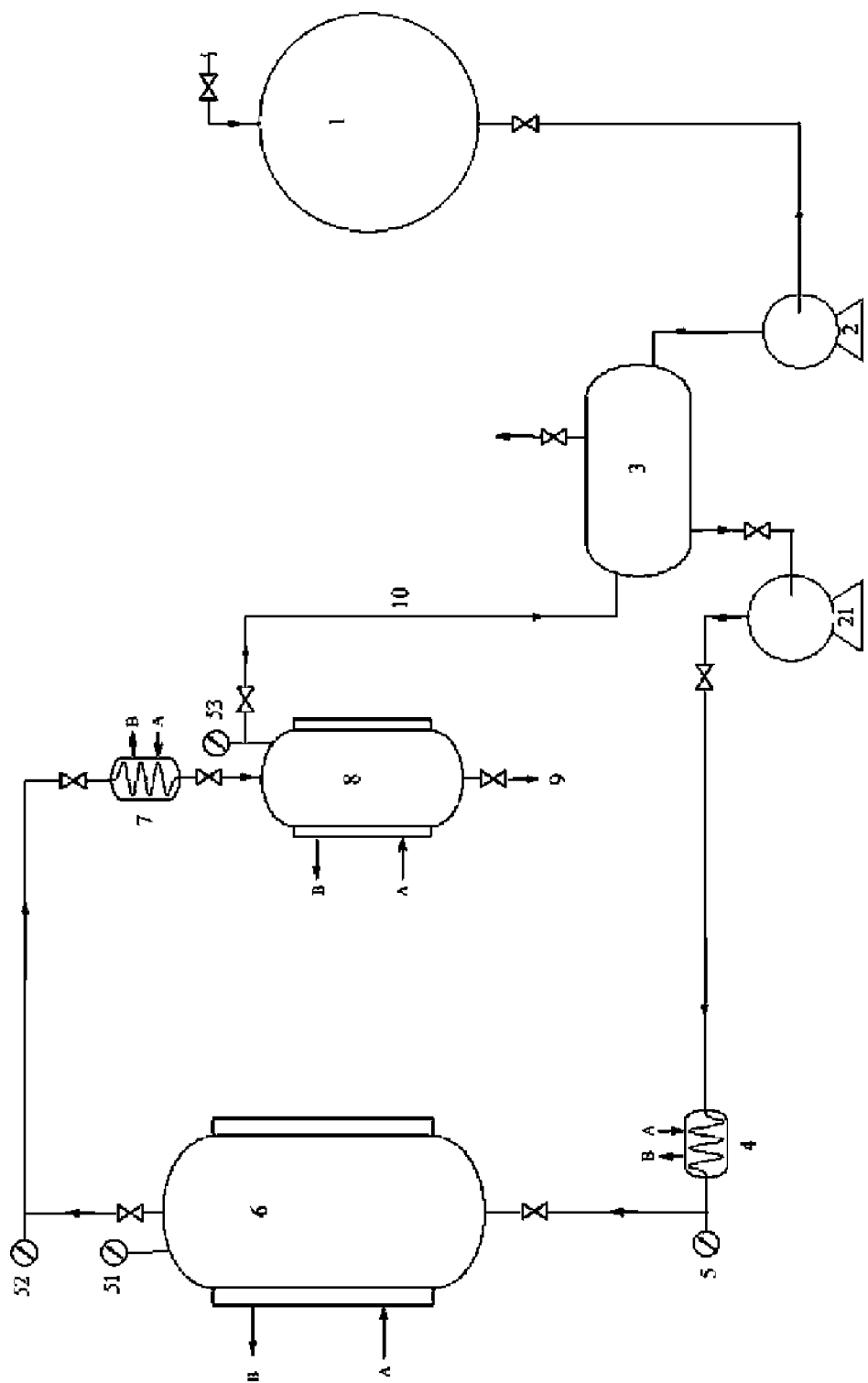

METHOD OF PREPARATION AND ISOLATION OF BETULIN DIACETATE FROM BIRCH BARK FROM PAPER MILLS AND ITS OPTICAL PROCESSING TO BETULIN

This application is a 371 of PCT/CZ2008/000004 filed Jan. 9, 2008.

TECHNICAL FIELD

The invention relates to a method of preparation and isolation of betulin diacetate from birch bark from paper mills and its optional processing to betulin.

BACKGROUND ART

Betulin is a natural pentacyclic triterpene, which is inter alia contained in varying amounts in the outer layers of the bark of birch trees (Betula sp.). Betulin is also an important commodity, particularly in cosmetic and pharmaceutical industry, for its various biological effects (Dzubak, P.; Hajduch, M.; Vydra, D.; Hustova, A.; Kvasnica, M.; Biedermann, D.; Markova, L.; Urban, M.; Sarek, J. Nat. Prod. Rep. 2006, 23, 394-411). Betulin is used either as such or in the form of its derivatives and compounds. Birch bark is easily available in huge amounts, because it is a waste product in paper and cellulose production in northern countries, where almost exclusively birches are processed (Jääskeläinen P.: Paperi-ja Puutavaralehti 1981, 10, 599-603). Daily, 40 tons of crude birch bark are produced worldwide, this bark is at present used only as a cheap fuel 5-7 USD/ton, 7-11 MJ/kg (Krasutsky P.: Nat. Prod. Rep. 2006, 23, 919-942).

The rigid skeleton of betulin is composed of 30 carbon atoms and is substituted only with two hydroxy groups, thus, as a lipophilic organic compound, it is almost insoluble in water and for the extraction thereof from a natural material, it is necessary to use other solvents. Most often, various organic solvents are used (e.g. butan-1-ol in RU2234936, toluene in RU2192879, petrolether in RU2194120, or lower alcohols—methanol, ethanol, isopropyl alcohol in RU2674867), in which betulin is more soluble at a higher temperature and after concentrating the extract, it can crystallize from the extract. In these solvent extractions, usually a ground birch bark is extracted with a hot solvent, the extract is then concentrated and after cooling down, crude betulin crystallizes from the extract. The extractions are often combined with washing with lyes in order to remove admixtures of acids (US2003153776, RU2270202, RU2270201). Chemical modification of the birch bark, either by oxidation agents or by acids, is used for the preparation of various betulin derivatives and the resulting derivatives are directly extracted by solvents such as diethyl ether or dichloromethane etc., which are present in the reaction mixture together with the bark (U.S. Pat. No. 6,280,778). This method firstly does not allow to obtain betulin from the birch bark, and then, it is very non-ecological and non-economical, because it uses substantial amounts of toxic organic solvents and produces a waste birch bark contaminated with oxidative and other process waste products. Another modern possibility to isolate betulin from birch bark is its supercritical extraction with carbon dioxide or with an admixture of methanol, ethanol or acetone (CN1634972, US2005158414), or eventually, these extraction techniques are combined with an activation of the bark by steam (RU2074867) or superheated steam (Kuznetsov B. N., Levdanski V. A., Polezhaeva N. I.: Khim. Rastit. Syr'ya, 2004, 2, 21-24), optionally in combination with ultrasound (RU2264411). Apart from the extraction methods of betulin isolation, also a sublimation method is known (Pakdel H., Murwanashyaka J. N., Roy C.: J. Wood CHem. Technol. 2002, 22, 174-155), which is characterized by the use of high vacuum and high temperatures, which provides a low yield of betulin. Only one patent document US2005158414 deals with the concentration of the birch bark component containing mainly the outer layers of the birch stem, which is based on a pneumatic separation by compressed air or on a separation through a mesh.

At present, a substantial ecological pressure is put on technologies in general, and pharmaceutical technologies in particular, not to harm the environment, i.e. not to use toxic substances and not to produce a toxic waste. Of course, industrial technologies must be ecological and economical at the same time. The above-mentioned solvent extraction methods of betulin production from the birch bark do not fulfil particularly the ecological criteria, because they use large volumes of toxic and flammable organic solvents, which cannot be fully regenerated, hence, at once waste solvents are produced and the bark after the extraction is soaked with these solvents. Furthermore, the thus obtained crude betulin has the purity of only 75-85%, contains a large amount of ballast admixtures (triterpenoids, fatty acids, etc.), is coloured and it is necessary to refine it before a further use, which is expensive. Supercritical (SC) methods fulfil high ecological requirements only partly, because in order to achieve sufficient extraction yield, it is necessary to use a mixture of carbon dioxide with organic solvents (e.g. ethanol, methanol; US2005158414) and relatively long extraction times. The betulin isolation from the extract and organic solvent recycling is thereby complicated. The SC extract has the purity of about 80%, contains a substantial fraction of low-molecular substances—fats, waxes, fatty acids, suberinic acids, triterpenoids and also dyestuffs. With regard to high operational costs for the SC extraction and the necessity of refining the SC extract, this method is very costly.

For the above listed reasons, it is apparent that the above-mentioned methods of production of the important triterpene betulin are not optimal, because they do not fulfil high ecological or economical requirements for modern technological processes. The aforementioned disadvantages are solved by the present invention, which connects the supercritical extraction with a chemical modification of the raw material.

DISCLOSURE OF INVENTION

Object of the invention is a method of preparation and isolation of betulin diacetate from birch bark from paper mills and its optional further processing to betulin, wherein the birch bark is ground, mixed with two- to twenty-fold excess volume of water and is stirred so that all birch bark is dipped, then the fraction of the birch bark which floats on the surface is collected, said collected fraction is dried at the temperature in the range of from 50 to 85° C. and the betulin contained in the dried birch bark is then subjected to an acetylation reaction, after the acetylation the birch bark is dried at the temperature of from 50 to 100° C. and the formed betulin diacetate is then isolated from the birch bark by supercritical extraction of the birch bark with carbon dioxide at the pressure of 28-35 MPa and the temperature of from 50 to 100° C. and subsequently, the supercritical extract is recrystallized for direct use or for further processing.

It is an aspect of the invention that the birch bark is ground into particles having the size of 5 to 10 mm, preferably into particles having the size of 6 to 8 mm.

It is a further aspect of the invention that the birch bark is ground by knife mill with cross cutting.

In a preferred embodiment of the present invention, 0.01-0.1% v/v of a tenside is added during the mixing of the ground birch bark with two- to twenty-fold excess volume of water.

The birch bark from northern countries paper mills contains on average 4-6% w/w of betulin, because it contains a substantial fraction of dust particles, wood and branches. Before the grinding itself, it is necessary to separate the birch bark from these fractions. The birch bark must then be ground, preferably into particles having the size of 5 to 10 mm, more preferably into particles having the size of 6-8 mm. With regard to the tough and soft character of the bark, knife mills with cross cutting are most suitable for the grinding, which effectively grind the bark to the required particle size. In contrast, grinders and hammer mills are not suitable, because the grinding is very slow. The thus ground birch bark has the betulin content of on average 10-12%, which is too low for further processing, and therefore must be refined beforehand in order to increase the betulin content. The ground birch bark can be refined by mixing with two- to twenty-fold excess volume of water, preferably with the addition of 0.01-0.1% v/v of a tenside, and thorough mixing so that all raw material is dipped. The fraction floating on the surface is collected and after drying has the betulin content of 21-24%, while the fraction at the bottom contains usually up to 3-4% of betulin. By this fluming procedure, about 25-30% of the birch bark is obtained, which already contains 21-24% of betulin and is suitable for further processing.

It is an aspect of the present invention that betulin contained in the birch bark is acetylated to form betulin diacetate by treatment with acetic anhydride in the presence of a tertiary amine (e.g., triethylamine, pyridine, aminopyridine, dimethylaminopyridine, N,N-dimethylaniline or N,N-diethylaniline):

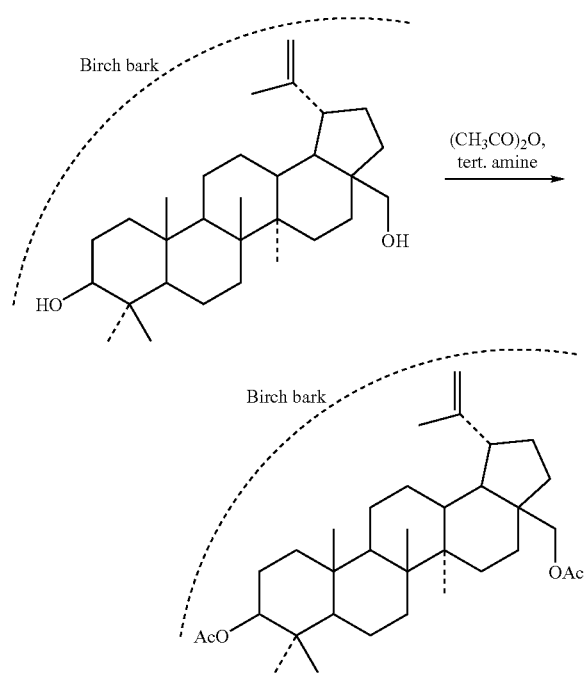

In a preferred embodiment, the tertiary amine is pyridine.

It is an aspect of another embodiment of the present invention that betulin contained in the birch bark is acetylated by ketene:

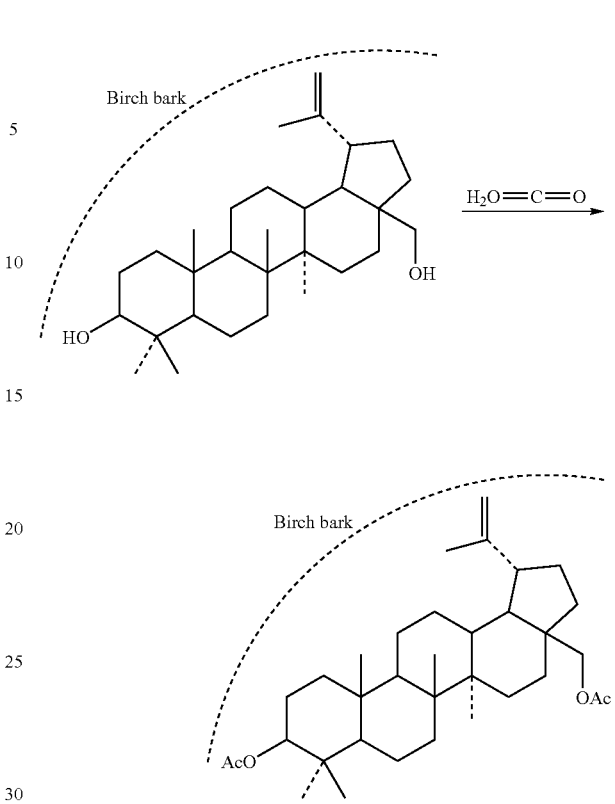

By the acetylation according to the present invention, the betulin present in the birch bark is converted into betulin diacetate, which is, due to its lower polarity, much more easily extractable by supercritical extraction (a lower temperature and a shorter extraction time) and very easily purifiable by crystallization. Furthermore, by this process, betulin diacetate can be obtained directly, while otherwise it must be prepared from betulin for the purposes of chemical syntheses. On the contrary, for the purposes of pharmaceutical and cosmetic industry, free betulin in pure form can easily be obtained by betulin diacetate hydrolysis.

It is a further aspect of the invention that the supercritical extraction of the thus chemically modified birch bark by carbon dioxide at the pressure of 28-35 MPa and the temperature of 50-100° C. according to the present invention can be performed e.g. in the supercritical extraction apparatus shown in FIG. 1. The obtained supercritical extract contains on average 85-87% w/w of betulin diacetate and is in the form of an off-white powder.

Another aspect of the invention is the crystallization of the supercritical extract, by which betulin acetate is obtained in the form of white powder having the purity of on average 95-97%, which is sufficient for chemical syntheses or hydrolysis thereof to form betulin. The crystallization can be carried out from a solvent selected from the group comprising chloroform, $C_1$ to $C_5$ alcohols, butanone and the mixtures thereof, preferably from butanone or from the mixture of chloroform and methanol. Free betulin can be obtained in the purity of >98% by basic hydrolysis of betulin diacetate. The hydrolysis can be carried out by e.g. alkali hydroxides, in $C_1$ to $C_5$ alcohols or preferably in their mixtures with aliphatic $C_6$ to $C_8$ or aromatic $C_6$ to $C_8$ hydrocarbons.

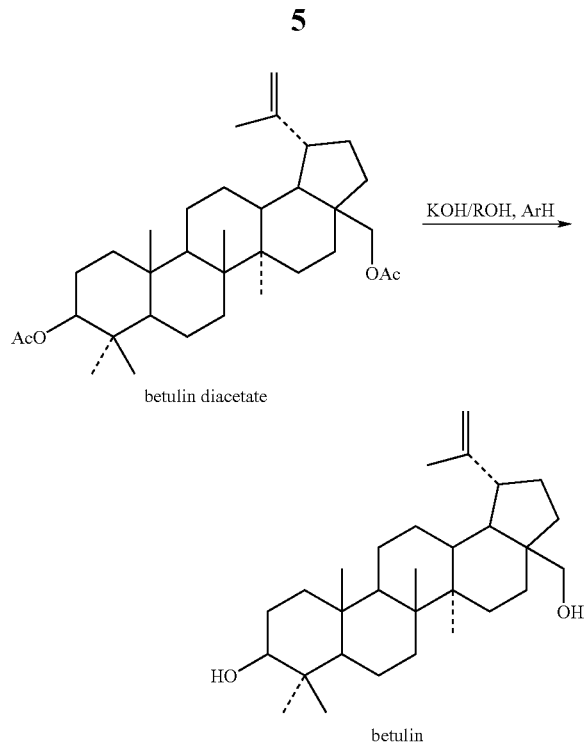

FIGURES

FIG. 1 shows the supercritical extraction apparatus. Reference numbers are as follows: 1—liquid $CO_2$ reservoir, 2, 21—compressors, 3—equalization reservoir of $CO_2$, 4—heater, 5, 51, 52, 53—manometers, 6—supercritical extractor, 7—condenser, 8—separator, 9—supercritical extract, 10—$CO_2$ recycling, A—heat transfer medium inlet, B—heat transfer medium outlet.

EXAMPLES

The method of isolation and production of betulin diacetate consists of the following steps: birch bark grinding, birch bark refining in order to increase the betulin content, chemical modification of the birch bark consisting in the acetylation thereof, super-critical extraction of the modified birch bark, crystallization of the supercritical extract, the result of which is betulin diacetate. Optionally, hydrolysis of betulin diacetate to betulin can follow.

For the determination of the betulin or betulin diacetate content, ethanol extraction or SCE were used, whereas the obtained extracts were subsequently analysed by HPLC-ESI technique. The sample for the determination was prepared by weighing 2.00 mg of the extract into 10 ml graduated flask, dissolving in ethanol and adding ethanol to 10 ml.

The analysis was carried out on the column ODS Hypersil 125×2.1 mm, 5 μm, Thermo EC, pre-column ODS 4.0×2.0 mm, Phenomenex, mobile phase A—100 mmol/l aqueous solution of ammonium formate R, pH adjusted to 5 by formic acid, B—acetonitrile, column temperature: 25° C., flow volume 0.3 ml/min, linear gradient elution 50-95% B, inlet volume 10 μl.

Melting points (m.p.) were determined on the melting point measuring apparatus Büchi B-545 and are corrected.

Specific optical rotations ($[\alpha]_D$) were determined on the polarimeter AUTOMATIC POLARIMETER, Autopol III (Rudolph research, Flanders, N.J.) and are shown in units of $[10^{-1}\ Deg\ cm^2\ g^{-1}]$, concentrations [g/100 ml] are shown for each specific optical rotation value.

NMR spectra were measured on the Varian $^{UNITY}$INOVA-400 apparatus ($^1H$ at 399.95 MHz, $^{13}C$ at 100.58 MHz) in the $CDCl_3$ solution. For $^1H$ MNR spectra, the inner standard was tetramethylsilane. Chemical shifts in $^{13}C$ NMR spectra were referenced against $\delta(CDCl_3)$=77.00 ppm. The signal multiplicity in $^{13}C$ NMR spectra was determined from DEPT spectra. Chemical shift values ($\delta$ scale) and interaction constants J (Hz) in $^1H$ NMR were determined by first order analysis. The chemical shifts were rounded to two decimal places, the interaction constants were rounded to one decimal place.

Example 1

Birch Bark Refining

Into a cylindrical pot, equipped with shaft stirrer and blow valve, 200 l of water of the temperature of 40-50° C. were poured, 40 ml-100 ml of cationactive or anionactive tenside were added. Then, the stirring was started and 40 kg of ground birch bark (particle size 6-8 mm) were slowly added, by a speed corresponding to the speed of dipping of the bark. After adding the whole amount of the birch bark, the stirring was continued for further 10 min and after that the stirrer was stopped. After 15 min, the bark fraction floating on the surface was collected, separated and the liquid was let to drain away. The refined bark was dried at 50-60° C. in a hot-air oven. 10.9 kg (27.9%) of the refined bark was obtained, containing 21-24% w/w betulin according to HPLC of its ethanolic extract.

Example 2

Chemical Modification of the Birch Bark by Acetic Anhydride

Into a cylindrical pot with blow valve, equipped with a sealable lid, 20 kg of the refined birch bark obtained by the method of example 1 were put in and 55 l of acetic anhydride containing 0.1-1.0% v/v pyridine were poured so that all bark is dipped under the surface. The content of the pot was then stirred with a stirrer and then the pot was sealed. The acetylation reaction took 5 days, whereas during the first three days, the content of the reaction vessel is spontaneously heated to 30-35° C. After this period, all the liquid was drained out of the vessel by the blow valve and 60 l of water of the temperature of 40-50° C. was added into the pot, the mixture was thoroughly stirred with the stirrer and the vessel was again sealed with the lid. After additional 5 days, the liquid was drained out and the bark was washed with 50 l of cold water and subsequently dried in hot-air oven at the temperature of 60-80° C. 19.3 kg of acetylated birch bark was obtained, which contains 15-18% w/w of betulin diacetate according to HPLC analysis of its supercritical extract.

Example 3

Chemical Modification of the Birch Bark by Ketene

Into a duplicated glass reactor with fused sintered glass equipped with gas medium inlet in the bottom and waste gas outlet in the upper part, 400 g of refined dry birch bark of Example 1 was put in and then the content of the vessel was heated by steam heating to the temperature of 50° C. Then, stream of ketene was fed into the vessel for 30 min, the ketene being generated from acetone by ketene lamp (Williams J. W., Hurd Ch. D.: J. Org. Chem. 1940, 5, 122-125). After finishing the ketene feeding, water steam was fed into the reactor for the period of 10 min. Subsequently, the reactor was taken apart and the acetylated bark was washed with water on a filter and dried in a hot-air oven at the temperature of 60-80° C. 411 g of acetylated birch bark was obtained, which contains 19-22% w/w of betulin diacetate according to HPLC analysis of a supercritical extract.

Example 4

Supercritical Extraction of the Chemically Modified Birch Bark

Rustless extraction liner having the volume of 100 ml was filled with chemically modified birch bark (23 g) and inserted into the extractor 6 of the supercritical extraction apparatus, which is shown in FIG. 1. After sealing the extractor 6, liquid carbon dioxide was let from the reservoir 1 into the piping leading to the compressor 2, from which it was led to equalization reservoir 3 and then through the compressor 21 led to the heater 4, where it was heated to the temperature 75° C. at the pressure 29-30 MPa (measured by the manometer 5). Thus heated and compressed carbon dioxide was then led to the extractor 6, into which the extraction liner was inserted. After reaching the working pressure of 29-30 MPa in the extractor 6 (manometer 51), the carbon dioxide is led away through the system of valves and the condenser 7 into the separator 8, in which the expansion occurs (manometer 53), whereas in the separator 8, the supercritical extract is deposited and carbon dioxide is recycled by recycler 10 into the equalizing reservoir 3. The carbon dioxide cycle in the apparatus is closed by that. The material was extracted in the supercritical extraction apparatus as described above at the pressure of 29-30 MPa, temperature of 75° C. for the period of 3 hours. At the end of the extraction, 3.47 g (15.1%) of white powder extract was obtained in the separator, which contains 81-86% w/w of betulin diacetate according to HPLC analysis.

Example 5

Crystallization of the Crude Supercritical Extract 7.80 kg of the supercritical extract prepared by the method of example 4 was dissolved at boiling in 37 l of butanone in glass duplicated reactor, equipped with a shaft stirrer, reflux condenser and blow valve. After dissolving all the material, the solution was concentrated while stirring to 28 l and the heating was stopped. At the temperature of the solution of 65° C., crystal seeds of betulin diacetate were added into the solution and when reaching the temperature of 50° C., the stirring was stopped. After cooling down to the laboratory temperature, the yielded crystals were filtered on a processing filter and washed with 1 l of butanone. After drying in a hot-air oven at the temperature of 60-70° C., 5.54 kg (71%) of betulin diacetate was obtained, having the m.p. of 222-223° C., $[\alpha]_D$+22° (CHCl$_3$; 0.4 g/100 ml), which has, according to HPLC analysis, the purity of 97.5-98.1%. $^1$H NMR spectrum of the obtained betulin diacetate, measured in CDCl$_3$ is as follows: 0.84 s, 0.84 s, 0.85 s, 0.97 s, 1.03 s, 1.68 s, 6×3H (6×CH$_3$); 2.04 s, 3H, 2.07 s, 3H (2×OAc); 2.44 ddd, 1H (J'=11.4, J"=10.9, J'''=5.8, H-19); 3.85 d, 1H (J=11.1, H-28a); 4.25 dd, 1H, (J'=11.1, J"=1.4, H-28b); 4.47 m, 1H (H-3α); 4.59 m, 1H (ΣJ=3.4, H-29E); 4.69 m, 1H (ΣJ=2.1, H-29Z). By concentrating the mother liquor to the volume of 10 l was after inoculation and cooling down obtained a second fraction of the crystalline betulin diacetate, which was also filtered on a processing filter and washed with 0.5 l of isopropyl alcohol. After drying in a hot-air oven at the temperature of 60-70° C., further 1.02 kg (13%) of betulin diacetate having the m.p. 222-224° C., $[\alpha]_D$+22° (CHCl$_3$; 0.4 g/100 ml), having, according to HPLC analysis, the purity of 96.8-97.2%. The overall yield of the crystallization is thus 6.56 kg of betulin diacetate (84%).

Example 6

Preparation of High-Purity Betulin from Betulin Diacetate

In a glass duplicated reactor, equipped with a shaft stirrer, reflux condenser, inlet tube and blow valve, 2.00 kg of betulin diacetate of example 5 was dissolved under stirring in the mixture of 10 l of toluene and 8 l of ethanol containing 700 g of potassium hydroxide. The reaction mixture was refluxed for 2 hours, then under heating filtered through a PP cloth and the filtrate was inoculated with pure betulin crystals. After cooling down, the crystallized betulin was filtered off on a processing filter, washed with 3 l of ethanol, 3 l of 50% ethanol and 30 l of boiling water and finally 5 l of boiling distilled water. The crystalline betulin was dried in a hot-air oven at the temperature of 70-75° C. for the period of 48 h. 1.12 kg (66%) of betulin in the form of fine crystalline power was obtained, having the m.p. 256-258° C., $[\alpha]_D$+16 (10% v/v CH$_3$OH in CHCl$_3$; 0.35 g/100 ml), which has the HPLC purity of 98.9-99.1%. $^1$H NMR spectrum of the obtained betulin measured in CDCl$_3$ with the addition of 10% v/v CD$_3$OD is as follows: 0.76 s, 0.83 s, 0.97 s, 0.98 s, 1.02 s, 1.68 s, 6×3H (6×CH$_3$); 2.39 ddd, 1H (J'=10.98, J"=10.8, J'''5.8, H-19β); 3.19 dd, 1H (J'=11.1, J"=5.2, H-3α); 3.33 dd, 1H (J'=11.0, J"=1.2, H-28a); 3.80 dd, 1H, (J'=10.8, J"=1.8, H-28b); 4.58 m, 1H (ΣJ=6.5, H-29E); 4.68 m, 1H (ΣJ=2.9, H-29Z). $^{13}$C NMR spectrum of the obtained betulin measured in CDCl$_3$ with the addition of 10% v/v CD$_3$OD is as follows: 14.74, 15.34, 15.96, 16.09, 18.28, 19.07, 20.81, 25.19, 27.02, 27.37, 27.97, 29.15, 29.73, 33.95, 34.21, 37.14, 37.29, 38.69, 38.84, 40.90, 42.70, 47.77, 47.77, 48.74, 50.38, 55.27, 60.53, 78.97, 109.68, 150.46. By concentrating the mother liquor to the final volume of 8 l was after inoculation and cooling down obtained a second fraction of the crystalline betulin, which was also filtered on a processing filter and washed in the same way as the first fraction. After drying in the hot-air oven at the temperature of 70-75° C. for the period of 48 h further 0.46 kg (27%) of the second fraction of betulin was obtained, having the m.p. 256-257° C., $[\alpha]_D$+16 (10% v/v CH$_3$OH in CHCl$_3$; 0.35 g/100 ml), which, according to HPLC analysis, has the purity of 98.7-99.0%. The overall yield of the hydrolysis is thus 1.58 kg of betulin (93%).

INDUSTRIAL APPLICABILITY

By the method of the invention, it is possible to obtain betulin diacetate of high purity from the waste birch bark from paper mills on industrial scale in an ecologically and economically advantageous way, and by the hydrolysis thereof it is possible to obtain betulin of high purity for use in pharmaceutical and cosmetic industry and in chemical syntheses.

The invention claimed is:
1. A method of preparation and isolation of betulin diacetate from birch bark from paper mills and its optional further processing to betulin, characterized in that the birch bark is ground, mixed with two- to twenty-fold excess volume of water and is stirred so that all birch bark is dipped, then the fraction of the birch bark which floats on the surface is collected, said collected fraction is dried at the temperature in the range of from 50 to 85° C. and the betulin contained in the dried birch bark is then subjected to an acetylation reaction, after the acetylation the birch bark is dried at the temperature of from 50 to 100° C. and the formed betulin diacetate is then isolated from the birch bark by supercritical extraction of the birch bark with carbon dioxide at the pressure of 28-35 MPa and the temperature of from 50 to 100° C. and subsequently, the supercritical extract is recrystallized for direct use or for further processing.

2. The method according to claim 1, characterized in that the birch bark is ground into particles having the size of 5 to 10 mm.

3. The method according to claim 2, characterized in that the birch bark is ground into particles having the size of 6 to 8 mm.

4. The method according to claim 1, characterized in that the birch bark is ground by knife mill with cross cutting.

5. The method according to claim 1, characterized in that 0.01-0.1% v/v of a tenside is added during the mixing of the ground birch bark with two- to twenty-fold excess volume of water.

6. The method according to claim 1, characterized in that betulin contained in the collected fraction of the birch bark is acetylated by treatment with acetic anhydride in the presence of a tertiary amine.

7. The method according to claim 6, characterized in that the tertiary amine is pyridine.

8. The method according to claim 1, characterized in that betulin contained in the collected fraction of the birch bark is acetylated by ketene.

9. The method according to claim 1, characterized in that the supercritical extract is recrystallized from a solvent selected from the group comprising chloroform, $C_1$ to $C_5$ alcohols, butanone and the mixtures thereof.

10. The method according to claim 9, characterized in that the solvent is selected from the group comprising butanone and a mixture of chloroform and methanol.

11. The method according to claim 1, characterized in that betulin diacetate is after the recrystallization processed to betulin by basic hydrolysis.

12. The method according to claim 11, characterized in that the hydrolysis is carried out by alkali hydroxide in a solvent selected from the group comprising $C_1$ to $C_5$ alcohols or their mixtures with aliphatic $C_6$ to $C_8$ or aromatic $C_6$ to $C_8$ hydrocarbons.

* * * * *